United States Patent
Doepker et al.

(10) Patent No.: US 8,006,577 B2
(45) Date of Patent: Aug. 30, 2011

(54) METHOD AND APPARATUS FOR TESTING FOR THE PRESENCE OF EXCESS DRIVERS IN A SURGICAL CARTRIDGE

(75) Inventors: Brian T. Doepker, Kalida, OH (US); David B. Erhart, Kalida, OH (US)

(73) Assignee: The Schnipke Family, LLC, Ottoville, OH (US)

( * ) Notice: Subject to any disclaimer, the term of this patent is extended or adjusted under 35 U.S.C. 154(b) by 555 days.

(21) Appl. No.: 12/117,878

(22) Filed: May 9, 2008

(65) Prior Publication Data

US 2009/0277288 A1 Nov. 12, 2009

(51) Int. Cl.
*G01N 19/00* (2006.01)
(52) U.S. Cl. ...................................................... 73/865.9
(58) Field of Classification Search .................. 73/865.9
See application file for complete search history.

(56) References Cited

U.S. PATENT DOCUMENTS

| | | | | |
|---|---|---|---|---|
| 5,653,928 A | * | 8/1997 | Schnipke | 264/138 |
| 5,836,147 A | * | 11/1998 | Schnipke | 59/71 |
| 6,158,205 A | * | 12/2000 | Schnipke et al. | 59/71 |
| 6,729,119 B2 | * | 5/2004 | Schnipke et al. | 59/71 |
| 7,207,168 B2 | | 4/2007 | Doepker et al. | |

* cited by examiner

*Primary Examiner* — Hezron E Williams
*Assistant Examiner* — Rodney T Frank
(74) *Attorney, Agent, or Firm* — Jason H. Foster; Kremblas & Foster

(57) ABSTRACT

A testing method and apparatus for determining whether surgical cartridges have excess drivers. A blade is disposed in the slots of the cartridge and displaced while it contacts the floor of the slot. If an excess driver is encountered, the blade is displaced away from the floor and this movement is detected, preferably by an electronic sensor. The apparatus includes a base plate to which a carriage is mounted, either directly or through other structural members. The carriage is configured to slide along a pair of parallel shafts, and is driven by a pneumatic ram or other linear prime mover. A tooling plate is moveably mounted to the carriage, and the blade is mounted to the tooling plate. Movement by the blade due to excess drivers results in movement by the tooling plate relative to the carriage, which is detected and recorded, such as by a computer.

14 Claims, 8 Drawing Sheets

METHOD AND APPARATUS FOR TESTING FOR THE PRESENCE OF EXCESS DRIVERS IN A SURGICAL CARTRIDGE

BACKGROUND OF THE INVENTION

1. Field of the Invention

This invention relates generally to an apparatus and a method for testing surgical cartridges into which discrete articles have been inserted, and more particularly for testing whether there are too many discrete articles in a surgical stapling cartridge.

2. Description of the Related Art

In the field of microsurgery, a surgical instrument having a cutting blade traverses a specific path through tissue. One feature of the surgical instrument is a single-use cartridge, shown in FIG. 1, that is a holder for surgical staples. The cartridge is an elongated plastic body with a longitudinal channel that serves as a guide for a surgical blade. The cartridge has rows of small staples on opposite sides of the channel, and these rows are aligned parallel to the guide channel. Drivers are inserted in apertures (also called "pockets") aligned with the rows in order to push the staples out of the cartridge and through the adjacent tissue. Before the blade has made its cut, each side of the incision is stapled together by displacing the drivers relative to the cartridge. This displacement forces the staples against an anvil on the opposing side of the surgical instrument as the cartridge and the anvil deflect the points of the staples into a clasping position.

There may be as many as fifty or more very small staples on each side of a two-inch incision. Each staple can be driven into the tissue to close the incision by the correspondingly small drivers. The task of inserting the drivers into the cartridge is labor-intensive due to the small size and number of the drivers and the apertures.

It is known in the prior art to insert drivers mechanically into surgical stapling cartridges, as shown in U.S. Pat. No. 5,836,147 to Schnipke, U.S. Pat. No. 5,653,928 to Schnipke, U.S. Pat. No. 6,158,205 to Schnipke et al., and U.S. Pat. No. 7,207,168 to Doepker et al., all of which are incorporated herein by reference. Workers manually position the cartridges, as well as the holders that contain the drivers and hold them relative to the machine, in the machines disclosed in these patents, and then actuate the machine to insert the tiny drivers into the pockets in the cartridges. After a fraction of the total number of drivers is inserted by one machine, the cartridge is then manually transported to the next machine, which inserts another fraction of the drivers. In U.S. Pat. No. 6,729,119 to Schnipke et al., which is incorporated herein by reference, a robotic loader is described for use in filling the cartridges discussed herein with the use of fewer workers than the prior art.

During the surgical procedure in which the surgical cartridges described above are used, the surgeon displaces two "sleds" longitudinally by manually depressing a trigger or otherwise actuating the surgical device that holds the cartridge. During this actuation, the sleds of the cartridge drive the drivers out of their home position, thereby driving the staples into the tissue, and a knife is displaced to make the incision. It is important that the knife make the incision either after, or while, the staples are driven into the tissue.

It is possible for too many, or for fewer than the required number of, drivers to be placed in a particular aperture during assembly of the cartridge. While the latter results in harm due to a staple not being driven at one region of the incision, the former results in a jammed instrument, thereby creating a severe danger to the patient. It is extremely difficult to determine whether too many or too few drivers are placed in a particular aperture, because of the relative size of the apertures and the drivers. There is, however, no way known to Applicants to rapidly and conveniently test a cartridge to determine if it has precisely the correct number of drivers in each aperture.

Therefore, there is a need for a machine for testing whether there are too many drivers inserted in apertures in a surgical cartridge.

BRIEF SUMMARY OF THE INVENTION

The invention is an improved device and method for testing surgical cartridges having at least one slot with a floor having at least one aperture into which at least one driver is inserted. An embodiment of the invention comprises a base configured to hold the cartridge stationary relative to the base. The floor of the cartridge is disposed along a predetermined line, such as a horizontal line. A carriage is movably mounted to the base for displacement relative to the base along a first path that is substantially parallel to the predetermined line. A prime mover is mounted to the carriage for displacing the carriage through the first path relative to the base, and a plate is movably mounted to the carriage for displacement relative to the carriage along a second path that is transverse to the first path. It is contemplated that the second path is vertical. A sensor is mounted, preferably to the carriage through other members, to detect movement of the plate relative to the carriage.

In a particularly preferred embodiment, the testing apparatus includes a base plate having an aperture and a carriage slidably mounted to the base plate for displacement along a substantially horizontal path. The linear prime mover, which can be a pneumatic ram, is mounted to the carriage for displacing the carriage relative to the base plate along the substantially horizontal path. A tooling plate is slidably mounted beneath the carriage for displacement relative to the carriage along a substantially vertical path. A plurality of planar blades is mounted to the tooling plate and extends downwardly toward the aperture. Means for detecting displacement of the tooling plate relative to the carriage is also included, such as an optical scanner. The sensor is preferably mounted to the carriage.

A method is also contemplated for testing surgical cartridges having a plurality of elongated, substantially parallel, spaced slots. The method includes the step of disposing the cartridge in an aperture of a base plate and displacing a carriage that is mounted to the base plate along a first path that is substantially parallel to the floors of the slots. The method also includes the step of extending the planar blades into the cartridge slots from the tooling plate moveably mounted to the carriage and detecting displacement of the tooling plate relative to the carriage. In a most preferred method, the planar blades are biased toward the respective floor, such as by the force of gravity Using the invention, a blade is disposed in the slot of the cartridge and displaced, such as along a horizontal path, while the blade contacts the floor of the slot, or more preferably the tops of the slightly protruding drivers. If there are excess drivers in the slots, the blade is displaced away from the linear path that the tops of the correctly inserted drivers form, and this movement is detected, preferably by an optical scanner. The tapered leading edges of the blades provide a vertical force when striking an excess driver, and that force lifts the blade. The carriage is mounted to the base plate, either directly or through other structural members, and is configured to slide along a pair of parallel shafts. The prime mover, which can be a pneumatic ram or other device, reciprocates the carriage. The tooling plate moveably mounted to the carriage, and the blades mounted to the tooling plate, are displaced transverse to the horizontal path when the device encounters an excess driver. Movement by the blade due to an excess driver results in movement by the tooling plate relative to the carriage, which is detected and recorded, such as by a computer.

Figure 1:
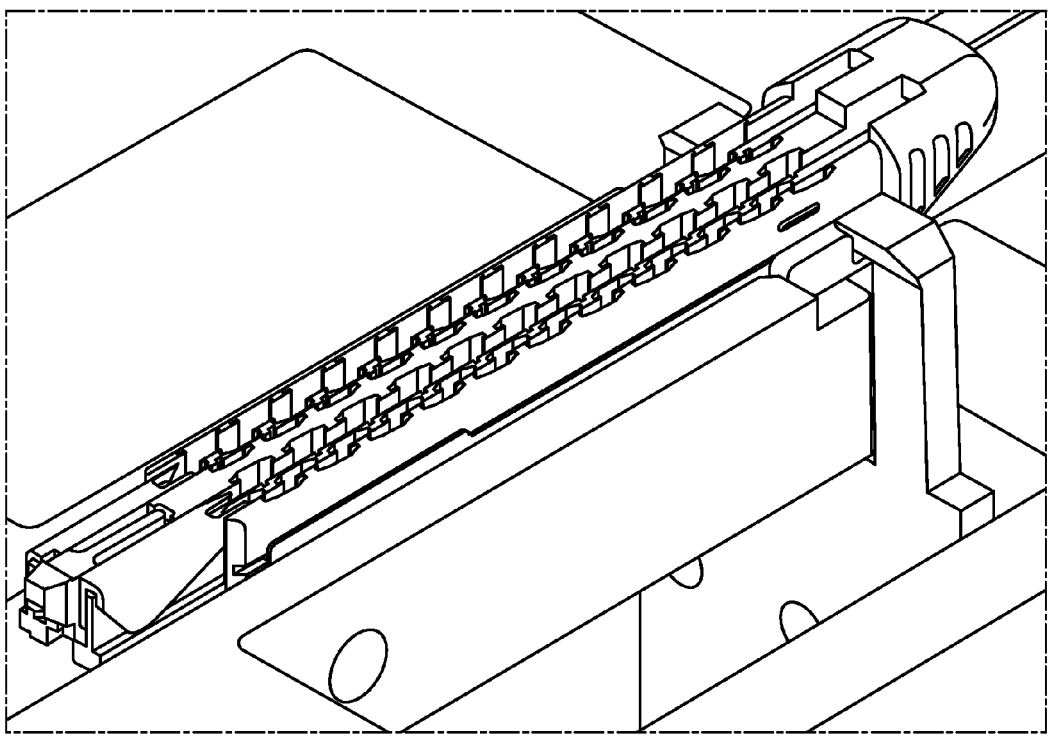
FIG. 1 is a view in perspective illustrating a prior art surgical cartridge with which the present invention is contemplated for use, among other cartridges.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected or term similar thereto are often used. They are not limited to direct connection, but include connection through other elements where such connection is recognized as being equivalent by those skilled in the art.

DETAILED DESCRIPTION OF THE INVENTION

Figure 2:
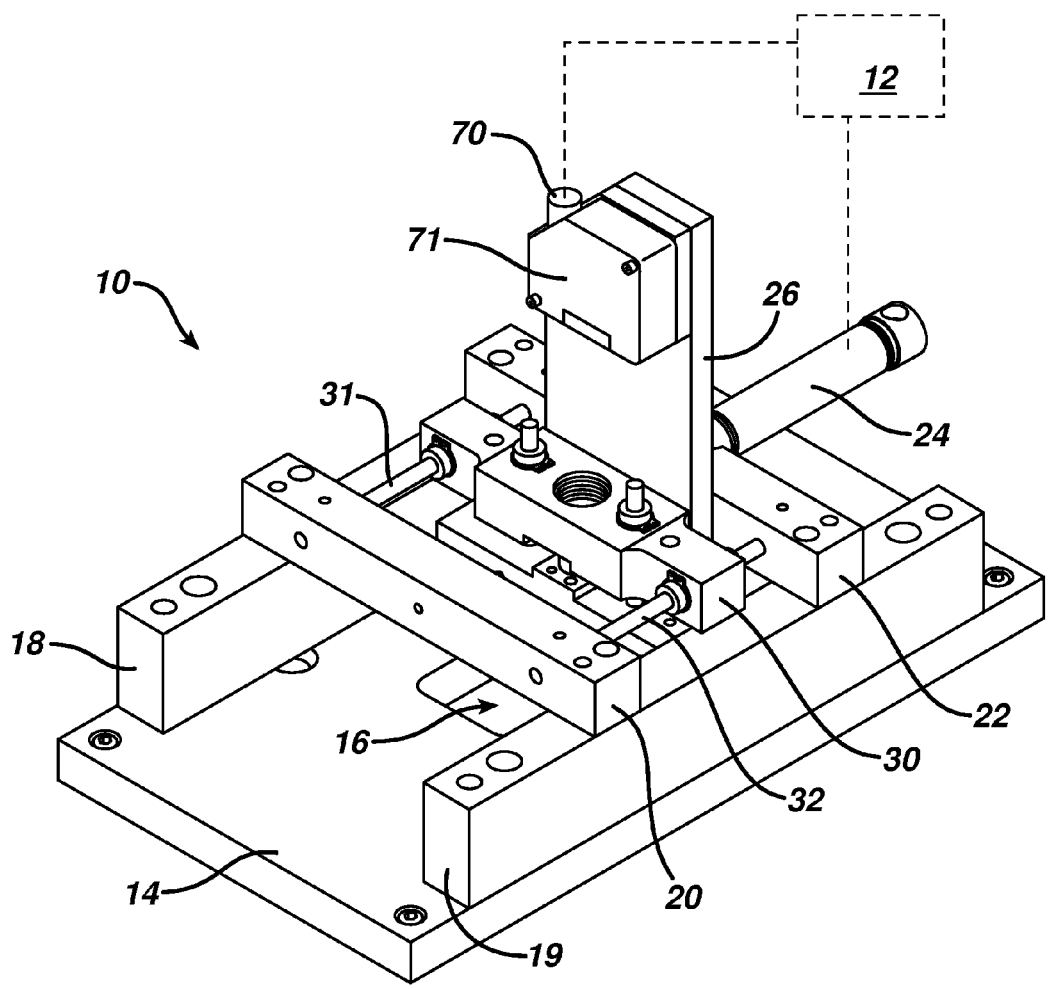
FIG. 2 is a view in perspective illustrating a preferred embodiment of the present invention.

The testing apparatus 10 shown in FIG. 2 is preferably positioned along an assembly line in which cartridges, such as that shown in FIG. 1, are assembled. Preferably, cartridges are mounted in pallets, as described in U.S. Pat. No. 6,990,796 to Schnipke, et al., which is incorporated herein by reference, and moved along an assembly line by a conveyor belt, as is known in the art. Such cartridges are fitted with drivers, one or more springs and other components during the assembly process. After complete assembly, or preferably nearly complete assembly, the cartridge is tested by the testing apparatus 10 in order to determine whether more than the required number of drivers has been inserted into the apertures of the cartridge. After testing, the cartridge is then designated, such as by recording the results of the test in the memory of a central computer 12, as either acceptable if it passed the test, or defective if it failed. This designation is then used to determine subsequent steps in the assembly process, as described in more detail below.

The testing apparatus 10 has a base plate 14 that is a rigid body, such as plate steel, with a central aperture 16. The components of the testing apparatus 10 are rigidly mounted to the base plate 14, which holds the components so that the components do not move relative to the base plate 14, other than those components described below as designed to move relative to one another.

Figure 3:
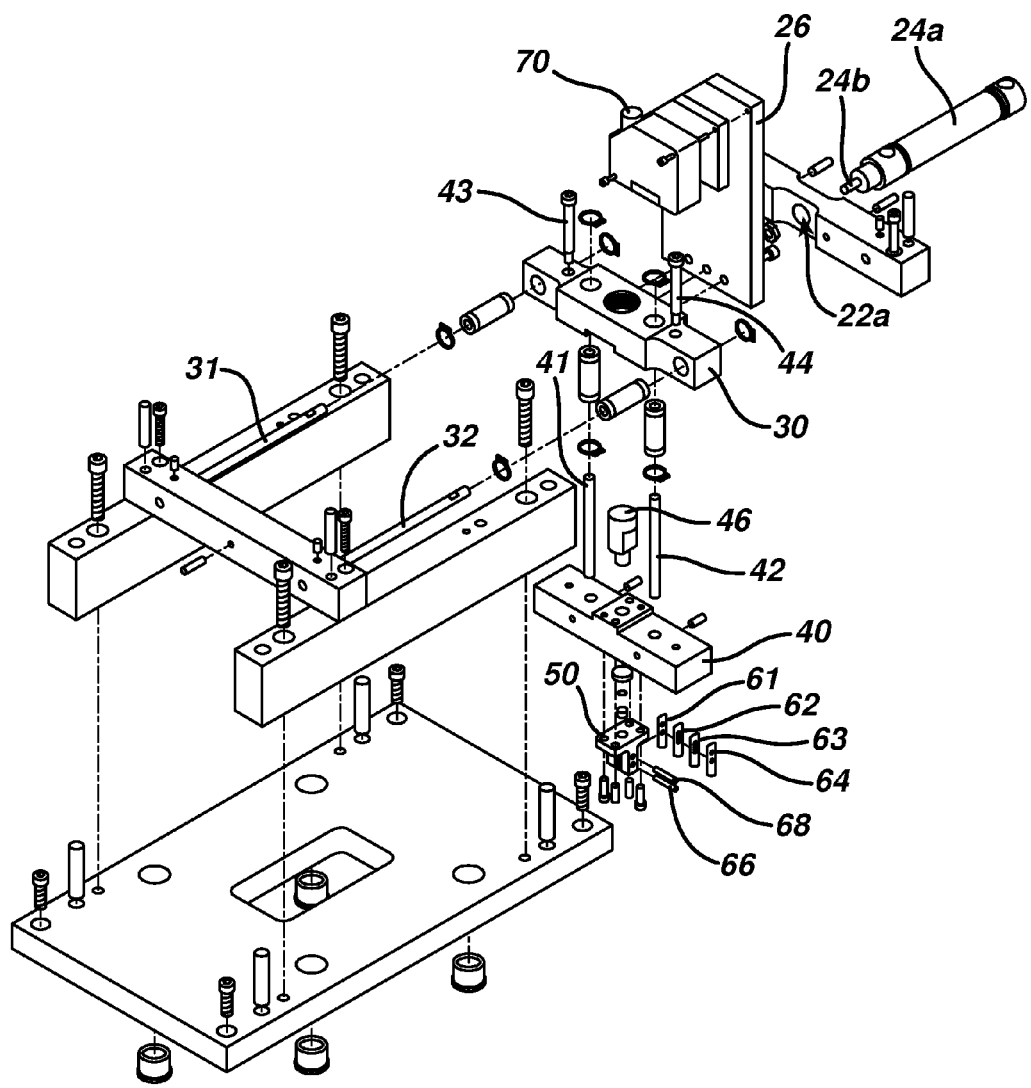
FIG. 3 is an exploded view in perspective illustrating the embodiment of FIG. 2.

The risers 18 and 19 are mounted to the base plate 14 by fasteners, such as screws as shown in FIG. 3. The shuttle support 20 and the shuttle cylinder mount 22 are screwed to the risers 18 and 19 to prevent relative movement. The cylinder 24 is mounted to the shuttle cylinder mount 22 by fixing the housing 24a (FIG. 3) thereof onto the shuttle cylinder mount 22. The cylinder 24 is preferably a conventional linear prime mover, such as an electric motor or pneumatic/hydraulic ram, but could be any drive mechanism that applies a linear, reciprocating force. The cylinder rod 24b extends through an aperture 22a formed in the shuttle cylinder mount 22 and attaches to the cylinder mount 26. The aperture 22a has a larger diameter than the rod 24b so that the rod 24b can extend through the aperture 22a and move therein without substantial resistance. Thus, actuation of the cylinder 24 causes the rod 24b to extend and retract in a conventional manner, thereby exerting a force on the cylinder mount 26, as is described below.

The cylinder mount 26 is rigidly mounted to the carriage 30, which is slidably mounted to the smooth, cylindrical shafts 31 and 32. The shafts 31 and 32 are rigidly mounted at opposing ends to the shuttle support 20 and the shuttle cylinder mount 22, which thereby retain the shafts 31 and 32 in fixed positions relative to the base plate 14. Conventional linear bearings mounted in apertures formed on the carriage 30 slidably receive the shafts 31 and 32. This configuration permits the carriage 30 to slide along the shafts 31 and 32 in a path defined by the substantially parallel axes of the shafts 31 and 32. The rod 24b is preferably parallel to the shafts 31 and 32. This path is preferably substantially horizontal, although it is contemplated that the path can be other than horizontal. It will become apparent that, through actuation of the cylinder 24, the cylinder mount 26 and the rigidly attached carriage 30 are moved along the path defined by the shafts 31 and 32 without substantial resistance.

It should be noted that terms such as "front," "rear," "top," "bottom," "horizontally," "vertically," "laterally," "longitudinally," "above" and "below" are used herein to describe the relative position and orientation of various components of the invention, all with respect to the geometry and orientation of the apparatus 10 in an operable orientation, which is shown in FIG. 2. This terminology includes the words specifically mentioned, derivatives thereof, and words of similar import, as understood by a person having ordinary skill in the art.

Beneath the carriage 30 is a tooling plate 40, which is best viewed in FIG. 3. The tooling plate 40 is suspended from the carriage 30 on a pair of shafts 41 and 42 that extend upwardly from rigid connection to the tooling plate 40 into linear bearings mounted in the carriage 30. The bearings permit the shafts 41 and 42 to slide without substantial resistance through the carriage 30 along a path that is substantially parallel to the substantially parallel axes of the shafts 41 and 42. In the preferred embodiment, the shafts 41 and 42 are vertically oriented, and the tooling plate 40 is thus biased toward a downward position by the force of gravity. This places the path of movement of the tooling plate 40 substantially perpendicular to the path of travel of the carriage 30 in the embodiment shown. It is contemplated that the paths of these bodies can be at various angles to one another, and that a bias of the tooling plate 40 toward one position can be induced by a mechanical spring or other equivalent.

A lower limit to downward travel of the tooling plate 40 is defined by the screws 43 and 44, which mount rigidly to the tooling plate at their lower ends with smooth shafts that extend upwardly therefrom through slightly larger apertures in the carriage 30. The screws 43 and 44 terminate in conventional screw heads that are larger than the apertures through which the screws 43 and 44 extend. Thus, the tooling plate 40 can be displaced upwardly from its start position (shown in FIG. 6) by a force applied to the tooling plate 40 that has an upward component, but it cannot be displaced downwardly farther than the start position without removing the screws 43 and 44.

Figure 5:
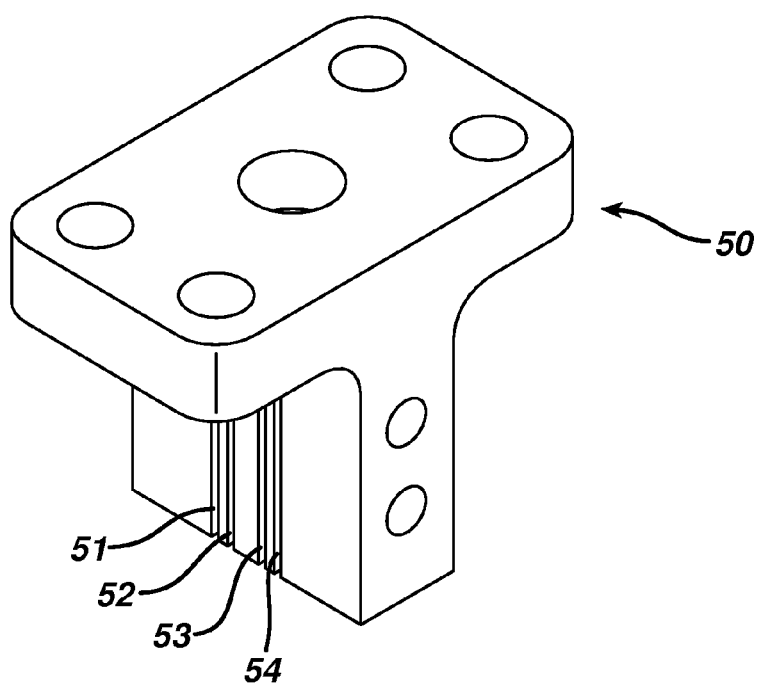
FIG. 5 is a view in perspective illustrating a preferred blade mount.

A blade mount 50, which is illustrated alone in FIG. 5, is rigidly mounted to the underside of the tooling plate 40, as illustrated in the exploded view of FIG. 3. The blade mount 50 has four slits 51, 52, 53 and 54 formed therein that are preferably planar and substantially parallel to one another. The number of slits 51-54 formed in the blade mount 50 is not critical, and embodiments are contemplated that have one, two and six and more slits. The slits 51-54 are preferably spaced apart precisely the same distance as the slots formed in the cartridges that will be tested by the testing apparatus 10.

Four blades 61, 62, 63 and 64 are mounted to the blade mount 50 with one blade in each of the slits 51-54, respectively, and aligned substantially parallel to the slits 51-54. The blades 61-64 are thin, substantially planar bodies that are preferably made of steel or other strong material, and are substantially equal in thickness to the slits 51-54 in which the blades are mounted. As described in relation to the slits, the number of blades is not critical, except that it is preferred to have one blade for every cartridge slot. Preferably, the pins 66 and 68 extend through, and frictionally fit within, apertures in the blade mount 50 that are aligned with apertures in the blades 61-64, thereby rigidly fixing the blades 61-64 to the blade mount 50. The blades 61-64 preferably have a thickness less than the width of the slots in the cartridges and a length greater than the slot depth.

Figure 4:
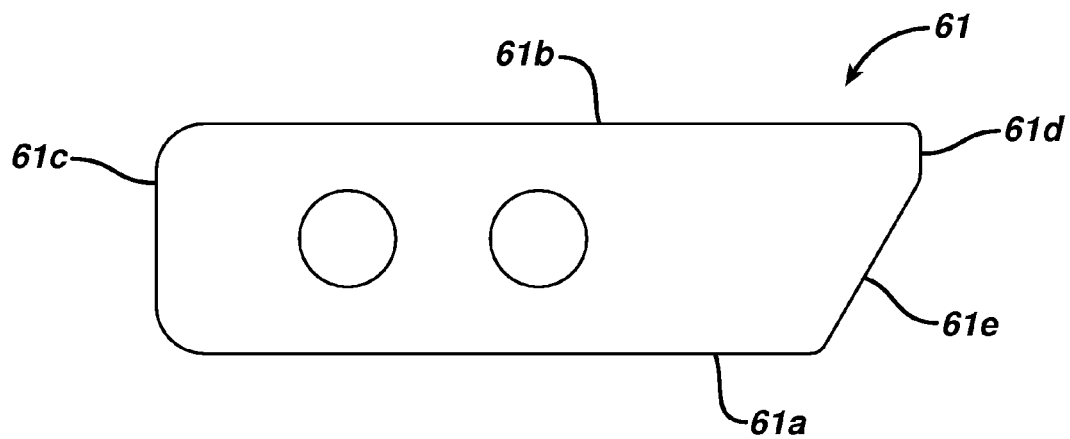
FIG. 4 is a side view illustrating an exemplary blade used with the present invention.

The blade 61 is representative of the blades 62-64, and is shown in greater detail in FIG. 4. The blade 61 has a front edge 61a, a rear edge 61b, a top edge 61c and a bottom edge 61d. A tapered edge 61e angles relative to the bottom edge 61d by approximately 30 degrees and when the blades 61-64 are mounted with their bottom edges facing downwardly, the tapered edges are positioned to face toward the shuttle support 20. The angle of the tapered edge 61e can vary as will be understood by the person having ordinary skill from the description of the invention.

The invention thus operates to displace the carriage 30, with the tooling plate 40 and attached blades 61-64, through a preferably horizontal path above the base plate 14, and preferably above the aperture 16 thereof. During this horizontal displacement, the tooling plate 40 and its attached structures are in the starting position beneath the carriage 30, but can be displaced upwardly if a sufficient force is applied to the blades 61-64.

Figure 6:
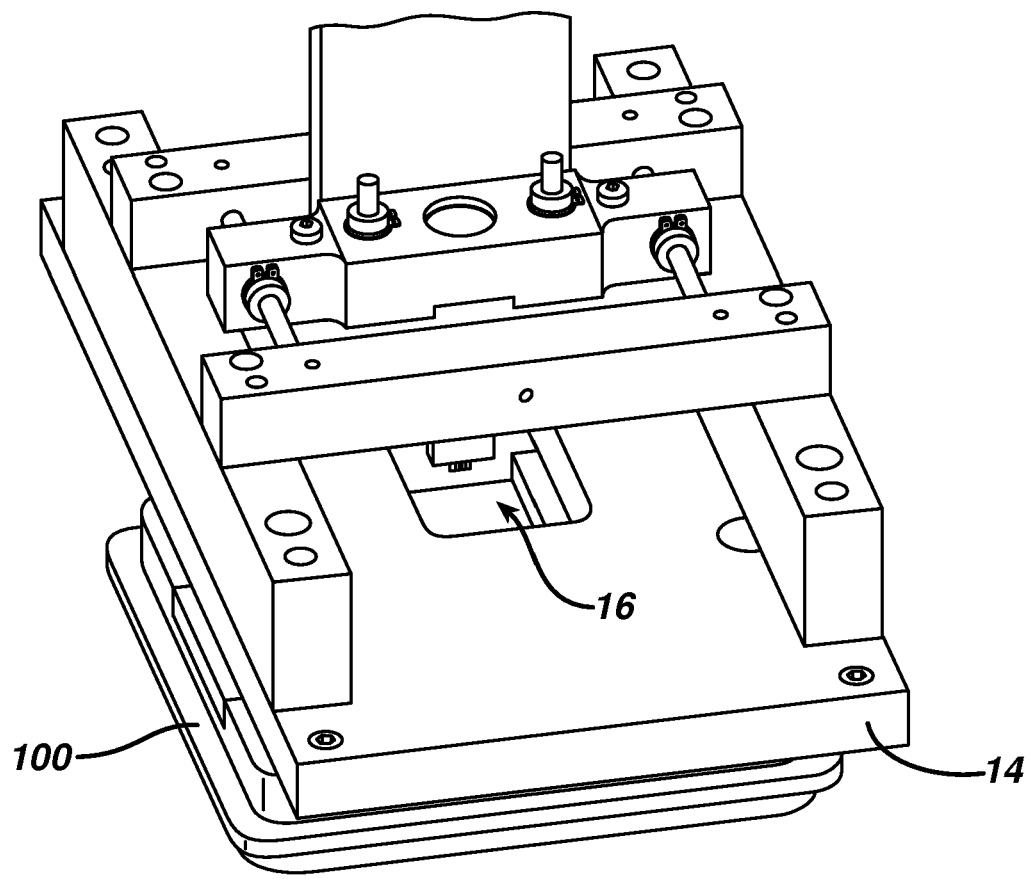
FIG. 6 is a view in perspective illustrating an embodiment of the present invention in a first portion of a preferred process.

The process of testing a cartridge includes the step of disposing a pallet 100, on which the cartridge is mounted, beneath the base plate 14 to align with the base plate 14 as shown in FIG. 6. The pallet 100 is raised from a lower position (FIG. 6) to a higher position (FIG. 7) by a conventional linear prime mover (not shown), such as a pneumatic ram, with a driven structure that contacts the pallet and displaces it upwardly. This action causes the upper surface of the pallet to engage the underside of the base plate 14, such as by tapered pins extending from the pallet into receptive sockets on the base plate 14 which thereby precisely align the pallet 100, and therefore the cartridge precisely positioned thereon, with the base plate 14 and all of its attached components.

Figure 7:
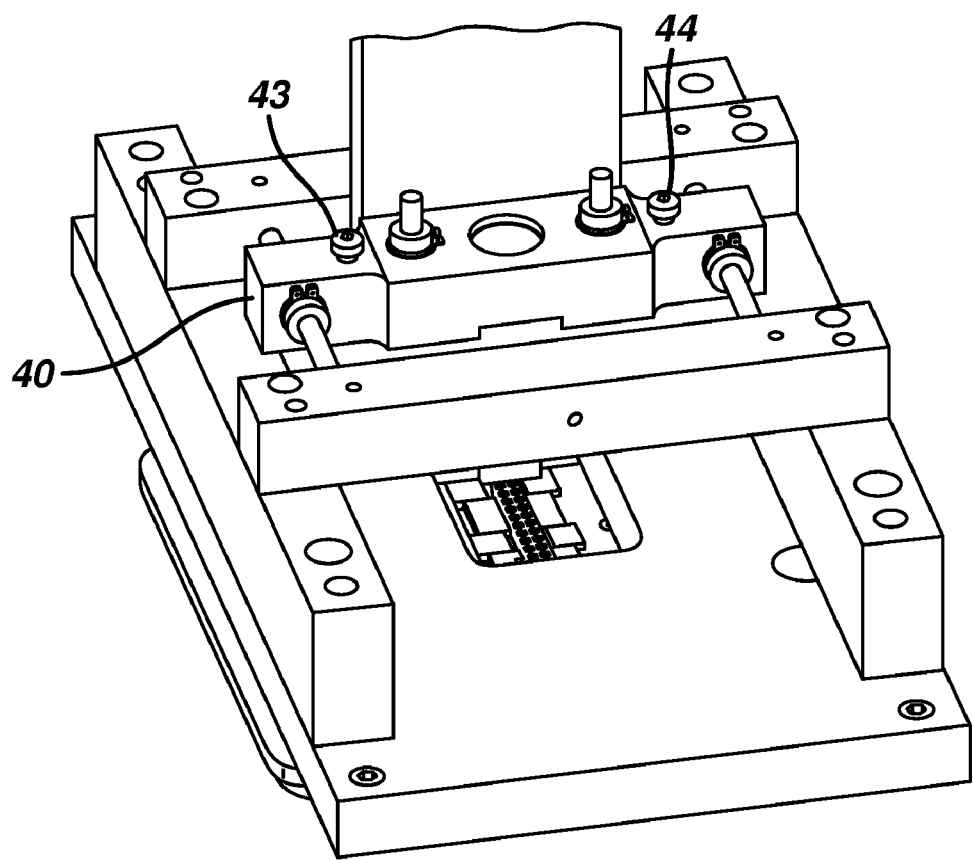
FIG. 7 is a view in perspective illustrating an embodiment of the present invention in a second portion of a preferred process.

When the pallet 100 is lifted to its extreme height, the cartridge on the pallet 100 protrudes at least partially through the aperture 16. The blades 61-64, which are aligned longitudinally with the slots of the cartridge, are thus inserted at one end of the slots of the cartridge. Contact is preferably first made between the lower edges of the blades and the slightly protruding tops of the correctly seated drivers. This contact raises the blades 61-64, and the connected tooling plate 40 and screws 43 and 44, upwardly a small distance, as shown in FIG. 7.

Once the cartridge is precisely located, the cylinder 24 is actuated to displace the carriage 30 substantially horizontally along the shafts 31 and 32, which correspondingly displaces the tooling plate 40 and attached blades 61-64 along a horizontal path. The blades 61-64 (not visible in FIG. 8, but which are beneath the tooling plate 40) are displaced along a substantially horizontal path through the slots in the cartridge with their tapered edges leading the blades as they progress through the slots. It is preferred that the blades 61-64 are driven through a path having a length substantially equal to the length of the slots, but it is contemplated that the path length must be at least as long as the portions of the slots that have apertures in which drivers could be inserted.

When precisely aligned with the slots in the cartridge, the blades 61-64 are displaced through the slots in a manner that causes little to no resistance due to scraping of the sides of the blades against the walls of the slots. As the blades 61-64 are displaced through the slots, the lower edges of each blade contact the tops of the drivers, which, in a cartridge having correctly seated drivers, are aligned along a line that is parallel to the lowest extreme surface defining the slots, herein referred to as "floors". The floors of the slots have the apertures into which drivers are inserted. The tops of the drivers define the lower limit of travel of the blades 61-64 in the slots, and preferably form a line that is substantially parallel to the floor of the respective slot.

If the drivers are seated correctly, the lower edge of each blade slides along the corresponding tops of the drivers in that slot. However, if a driver protrudes above the line connecting the tops of the drivers due to being seated in an aperture incorrectly, then the leading tapered edge of the blade encounters the excessively protruding driver and applies a downwardly directed force to the driver. This downward force fully inserts an incompletely seated driver into a seated position.

Due to the mass of the tooling plate 40 and its attached components, an unseated driver will not cause the vertical force applied by the blade to the driver to lift the tooling plate 40 appreciably. However, when there is an excess driver in an aperture, the driver protruding from that aperture cannot move downwardly under the vertical force applied by the blades 61-64 and attached components, because there is no space for that driver to be displaced into. Instead, the protruding driver abuts another driver. Therefore, when there is an excess driver that protrudes above a line connecting the tops of the correctly seated drivers in the cartridge slot, the tapered leading edge of the blade that contacts the extremely protruding driver applies a vertical force that causes the blade to raise up a distance equal to the height that the driver protrudes above the correctly seated drivers. This therefore raises the attached tooling plate 40 over the protruding driver through the path defined by the shafts 41 and 42.

When the tooling plate 40 encounters an excess driver, the path the tooling plate 40 follows is altered from exclusively horizontal when the blades slide along the tops of the correctly seated drivers. Instead, a vertical component is introduced into the path of travel of the tooling plate 40. This vertical component is detected by a sensor, such as the sensor 70, and recorded by the connected central computer 12. The sensor 70 is mounted to the block 71 that is rigidly mounted to the cylinder mount 26. The sensor 70 is preferably an optical scanner that is positioned directly above the post 46. The post 46 is rigidly mounted in the tooling plate 40 and extends through a slightly larger aperture in the carriage 30. Of course, any device that detects movement of a body can be used in place of the preferred sensor. Even a human being watching the tooling plate who visually notices vertical movement can substitute for the sensor 70.

The optical scanner detects the position of the top of the post 46 in a conventional manner and sends a corresponding signal to the central computer 12. In this configuration, as the tooling plate 40 and its attached post 46 move vertically, the sensor 70 detects this movement and signals the central computer 12. This signal is processed by the central computer 12 to designate the cartridge being tested as "defective" if the distance vertical moved by the tooling plate 40 exceeds a predetermined maximum. In a preferred embodiment, the sensor 70 detects the position of the post 46 from the time the cylinder 24 is actuated until a half cycle of reciprocation is traversed. Thus, movement in one direction from the starting point to the stopping point of the carriage 30 prior to returning to the starting point again.

In the preferred embodiment described above, the tooling plate 40 is at a lower, starting position when the cartridge is not yet contacting the blades. The tooling plate 40 is displaced upwardly slightly when the lowest edges of the blades 61-64 seat against and are lifted a small distance by the tops of the correctly seated drivers in the cartridge slots (as shown in FIG. 7) when the pallet 100 is in full contact with the base plate 14. The blades are driven through their horizontal path, and if no drivers protrude excessively, then the tooling plate 40 maintains substantially the same horizontal path during the entire stroke of the blades 61-64. The central computer 12 designates the cartridge being tested as acceptable when the tooling plate 40 is not lifted during this horizontal movement an amount greater than a predetermined maximum. However, if one or more drivers protrude excessively due to excess drivers in an aperture, and the blades 61-64, tooling plate 40 and post 46 are driven upwardly, this movement is detected by the sensor 70. The upward movement exceeding a predetermined maximum is recorded by the central computer 12, which uses logic programmed therein to designate the cartridge containing the protruding driver as defective.

Figure 8:
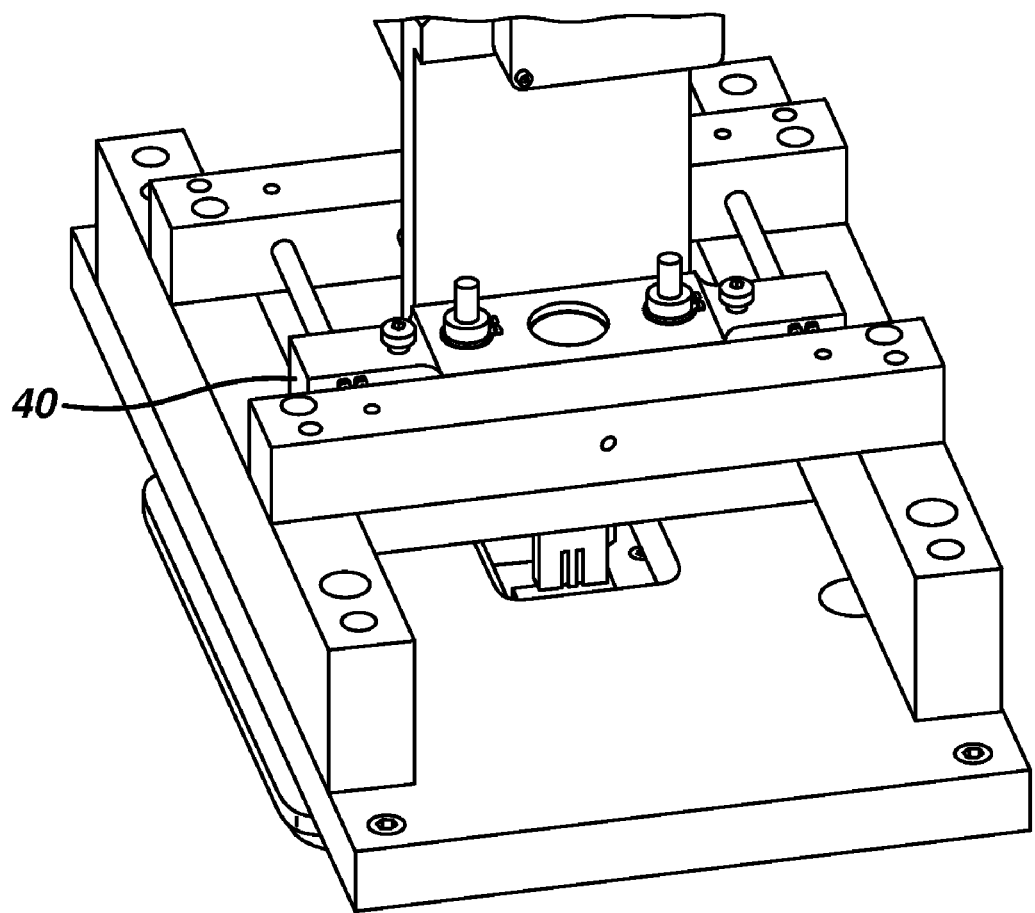
FIG. 8 is a view in perspective illustrating an embodiment of the present invention in a third portion of a preferred process.
Figure 9:
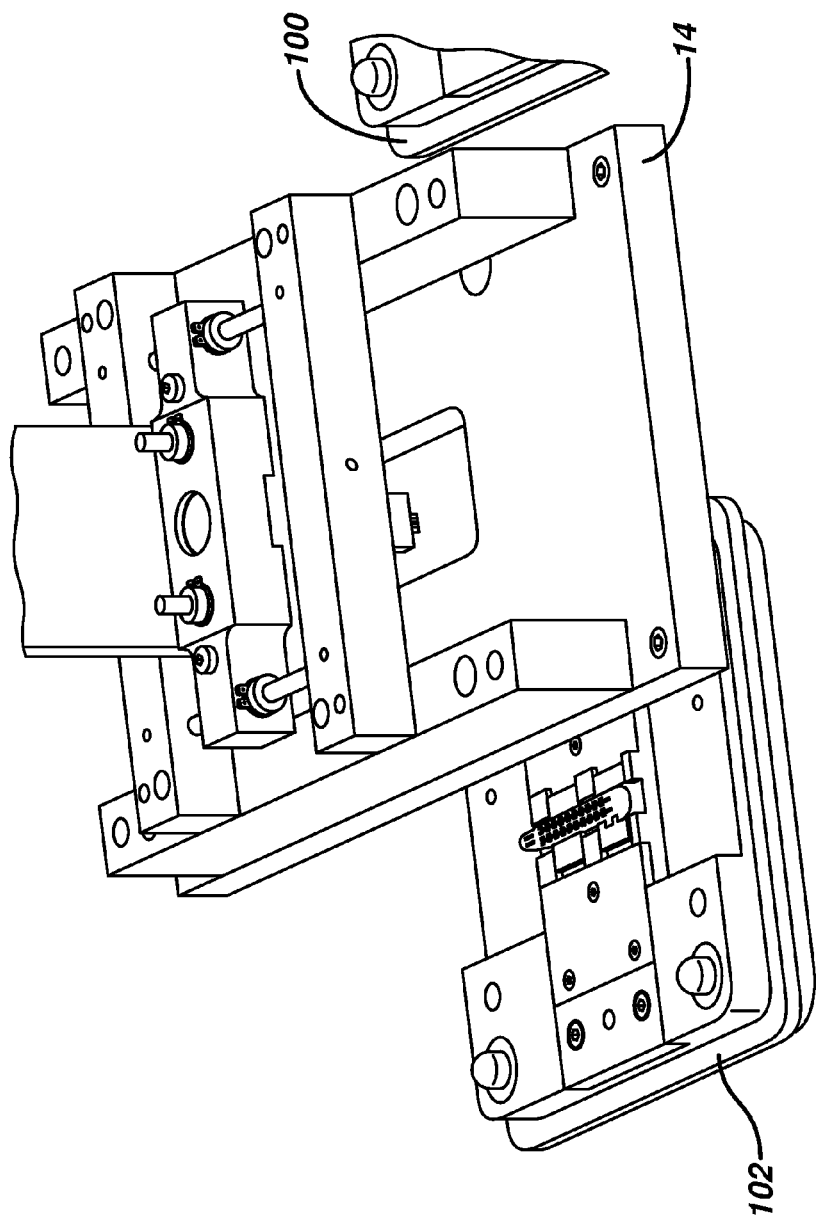
FIG. 9 is a view in perspective illustrating an embodiment of the present invention in a fourth portion of a preferred process.

When the full stroke of the carriage's horizontal displacement is complete, as shown in FIG. 8, the pallet 100 is lowered from the base plate 14 and carried away, as shown in FIG. 9, to be replaced by the next upstream pallet 102. It is preferred that the cylinder 24 drives the carriage 30 through the return half of the cycle (shown in FIG. 9) after the pallet 100 has been lowered and the attached cartridge has dropped below the lower face of the base plate 14, but before the next pallet is raised, in order to return the carriage 30 to the start position before the next cartridge is in position to be tested. While the carriage 30 is driven to the starting point, the next pallet 102 is conveyed to beneath the base plate 14 and raised upwardly to register with the base plate 14 after the carriage 30 is in the start position. This begins a new test cycle.

Any cartridge that is designated "defective" by the central computer 12 preferably has no additional components inserted therein during subsequent stations of the assembly line, and is removed at the end of the assembly process and discarded or recycled. Defective cartridges are removed so they are not mixed with cartridges that are designated acceptable. It is contemplated that defective cartridges can be removed from the assembly line immediately upon receiving the defective designation, and it is also contemplated that defective cartridges can have additional components added, if possible, and then removed at the end of the assembly process.

The blades 61-64 described herein are particularly advantageous, but could be replaced by narrow pins with wheels mounted at the lower ends thereof. Furthermore, ball-bearings at the lower end of pins are another type of blade that could be substituted for the blades described above. Additionally, although the bias of gravity is used herein, it is contemplated that the plane of movement of the carriage can be any orientation other than horizontal, and a bias by a mechanical spring or other device can bias the blades toward the floors of the cartridge slots.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. A testing apparatus for a surgical cartridge, the surgical cartridge having at least one slot with a floor, the floor having at least one aperture into which at least one driver is inserted, the apparatus comprising:
    (a) a base configured to hold said cartridge stationary relative to the base, wherein said at least one floor is disposed along a predetermined line;
    (b) a carriage movably mounted to the base for displacement relative to the base along a first path that is substantially parallel to the predetermined line;
    (c) a prime mover mounted to the carriage for displacing the carriage through the first path relative to the base;
    (d) a plate movably mounted to the carriage for displacement relative to the carriage along a second path that is transverse to the first path; and
    (e) a sensor mounted to detect movement of the plate relative to the carriage.

2. The testing apparatus in accordance with claim 1, wherein the carriage is mounted to the base through other members.

3. The testing apparatus in accordance with claim 1, wherein the first path is substantially horizontal.

4. The testing apparatus in accordance with claim 3, wherein the second path is substantially vertical.

5. A testing apparatus for a surgical cartridge, the surgical cartridge having a plurality of elongated, substantially parallel spaced slots, each slot having a floor with a plurality of apertures into which drivers are inserted, the apparatus comprising:
    (a) a base plate having an aperture;
    (b) a carriage slidably mounted to the base plate for displacement along a substantially horizontal path;
    (c) a linear prime mover mounted to the carriage for displacing the carriage relative to the base plate along the substantially horizontal path;

(d) a tooling plate slidably mounted beneath the carriage for displacement relative to the carriage along a substantially vertical path;
(e) a plurality of planar blades mounted to the tooling plate and extending downwardly toward the aperture; and
(f) means for detecting displacement of the tooling plate relative to the carriage.

6. The testing apparatus in accordance with claim 5, wherein the linear prime mover is a pneumatic ram.

7. The testing apparatus in accordance with claim 6, wherein the plurality of planar blades comprises four blades.

8. The testing apparatus in accordance with claim 5, wherein each blade has a lower edge configured to seat against its corresponding floor and a tapered leading edge.

9. A testing apparatus for a surgical cartridge, the surgical cartridge having a plurality of elongated, substantially parallel spaced slots, each slot having a floor with a plurality of apertures into which drivers are inserted, the apparatus comprising:
    (a) a base plate having an aperture;
    (b) a carriage slidably mounted to the base plate for displacement along a substantially horizontal path;
    (c) a linear prime mover mounted to the carriage for displacing the carriage relative to the base plate along the substantially horizontal path;
    (d) a tooling plate slidably mounted beneath the carriage for displacement relative to the carriage along a substantially vertical path;
    (e) a plurality of planar blades mounted to the tooling plate and extending downwardly toward the aperture; and
    (f) a sensor mounted to the carriage for detecting displacement of the tooling plate relative to the carriage.

10. The testing apparatus in accordance with claim 9, wherein the linear prime mover is a pneumatic ram.

11. The testing apparatus in accordance with claim 10, wherein the plurality of planar blades comprises four blades.

12. The testing apparatus in accordance with claim 9, wherein each blade has a lower edge configured to seat against its corresponding floor and a tapered leading edge.

13. A method for testing a surgical cartridge, the surgical cartridge having a plurality of elongated, substantially parallel spaced slots, each slot having a floor with a plurality of apertures into which drivers are inserted, the method comprising:
    (a) disposing the cartridge in an aperture of a base plate;
    (b) displacing a carriage that is mounted to the base plate along a first path that is substantially parallel to the floors;
    (c) extending a plurality of planar blades into the cartridge slots from a tooling plate moveably mounted to the carriage; and
    (f) detecting displacement of the tooling plate relative to the carriage.

14. The method in accordance with claim 13, further comprising the step of biasing the planar blades toward the respective floor.

* * * * *